United States Patent [19]

Nyman

[11] Patent Number: 5,397,340
[45] Date of Patent: Mar. 14, 1995

[54] METHOD AND ARRANGEMENT FOR IMPLANTING OR EXPLANTING AN INTRAVASCULAR CATHETER

[75] Inventor: Per Nyman, Djursholm, Sweden

[73] Assignee: Siemens Aktiengesellschaft, Munich, Germany

[21] Appl. No.: 58,443

[22] Filed: May 7, 1993

[30] Foreign Application Priority Data

May 12, 1992 [EP] European Pat. Off. ............ 92107995

[51] Int. Cl.⁶ .............................................. A61B 17/00
[52] U.S. Cl. ...................................... 607/116; 604/95
[58] Field of Search ................ 128/662.06; 607/125, 607/116; 604/95, 96; 606/194

[56] References Cited

U.S. PATENT DOCUMENTS

| | | |
|---|---|---|
| 3,352,303 | 7/1965 | DeLaney . |
| 3,665,928 | 5/1972 | Del Guercio .................. 604/95 |
| 4,749,376 | 6/1988 | Kensey et al. . |
| 4,854,325 | 8/1989 | Stevens . |
| 4,907,572 | 3/1990 | Borodulin et al. . |
| 5,041,124 | 8/1991 | Kensey . |

FOREIGN PATENT DOCUMENTS 0267539 11/1987 European Pat. Off. .
0310295  9/1988 European Pat. Off. .

*Primary Examiner*—William E. Kamm
*Assistant Examiner*—Scott M. Getzow
*Attorney, Agent, or Firm*—Hill, Steadman & Simpson

[57] ABSTRACT

A method and apparatus facilitate movement of a catheter through a blood vessel in a direction substantially parallel to the longitudinal extent of the catheter, by mechanically oscillating the catheter to impart movement at least to the distal end of the catheter in a direction substantially transversely to the longitudinal extent of the catheter. The oscillatory movement transverse to the longitudinal extent of the catheter continuously repels the catheter from the walls of the vessel in which the catheter is disposed, thereby reducing friction between the catheter and the blood vessel and making movement of the catheter within the vessel easier for implantation and explantation of the catheter.

18 Claims, 1 Drawing Sheet

METHOD AND ARRANGEMENT FOR IMPLANTING OR EXPLANTING AN INTRAVASCULAR CATHETER

BACKGROUND OF THE INVENTION

1. Field of the Invention

The invention relates to a method and arrangement for implanting or explanting an intravascular catheter which reduce friction between the catheter and the blood vessel through which the catheter is being moved.

2. Description of the Prior Art

The introduction of an intravascular catheter, for example a pacemaker electrode, into the body of a patient is impeded by friction between the catheter and the wall of the blood vessels accommodating the catheter. In order to reduce the friction, it is known to coat the electrode catheter with a lubricant.

Within a few months after the implantation, the electrode catheter becomes enclosed by a layer of connective tissue which anchors the electrode catheter in such a way that it is difficult, dangerous or even impossible to withdraw the catheter from the blood vessels accommodating it. Therefore, when an explantation of the catheter is not absolutely necessary it is required to weigh the risks associated with the explantation of the catheter against the risk to the patient in leaving the catheter in his body. If, by contrast, as in the case of an infection, an explantation of the catheter is absolutely necessary and the risk associated with the withdrawal of the catheter is too large, the withdrawal of the catheter requires the blood vessels accommodating it to be cut open.

An intravascular catheter is disclosed in U.S. Pat. No. 4,749,376 which has a tool at its distal end for removing deposits in blood vessels or for widening vasoconstrictions. Arranged at the proximal end of this known catheter is a motor whose rotary movement is transmitted by a control wire e interior of the catheter to the distal end thereof and is converted into an oscillating stroke of the tool in the direction of the longitudinal extent of the catheter.

Another intravascular catheter disclosed in U.S. Pat. No. 3,352,303, having an electromechanical transducer disposed at a proximal end of the catheter whose vibrational energy is transmitted, for example, via a wire or a liquid to the distal end of the catheter for the purpose of breaking up intravascular blood clots.

A similar catheter for removing vessel blockages is disclosed in U.S. Pat. No. 4,854,325, in which a control wire extends through the catheter and projects from the distal end of the catheter, and is set into an oscillating stroke by a motor at the proximal end of the catheter.

A common feature of these known catheters is that in each case, a stroke is generated at their distal end in the direction of the longitudinal extent of the catheter, so that obstructions in the path of introduction of the catheter can be removed. In these known catheters the friction between the catheter and the wall of the blood vessels accommodating the catheter is not reduced by the strokes. Moreover, in these known catheters there is the risk that the wall of the blood vessel accommodating the respective catheter will be pierced by the distal catheter tip. Finally, the above-named catheters are not provided for longer term implantation in the human body, so that the initially cited problems do not occur in connection with the explantation of the catheter.

SUMMARY OF THE INVENTION

It is an object of the present invention to provide a method and arrangement which facilitate the implantation and explantation of an intravascular catheter, wherein the risk of damage to the blood vessels accommodating the catheter simultaneously is reduced.

In accordance with the principles of the invention, the above object is achieved in a method for implanting and explanting a catheter by connecting the catheter to a mechanical oscillator which imparts movement, at least to the distal end of the catheter, transverse to the longitudinal extent of the catheter.

By setting the catheter into an oscillating movement at least in the region of its distal end transverse to its longitudinal extent, the catheter is continuously repelled by the vessel wall surrounding it, so that given a sufficiently high frequency of the oscillating movement the catheter effectively floats on the vessel wall. As a result, the friction between the catheter and the vessel wall surrounding it is substantially reduced, so that during implantation the catheter can easily be pushed through the blood vessels accommodating it. In a corresponding way, the explantation of the catheter is also facilitated, because the anchoring of the catheter in the vessel surrounding it is loosened by the oscillating movement and the friction is reduced during withdrawal of the catheter. In the cases of both implantation and explantation of the catheter according to title invention, the risk of damage to, or even piercing of, the blood vessels is minimized, since the oscillating movement is performed not in the direction of the longitudinal extent of the catheter, but transverse thereto.

In a modified version of the method according to the invention the oscillating movement is implanted to further regions if the catheter between its distal end and its proximal end. As a result, the friction between the catheter and the blood vessels accommodating it is reduced not only in the region of the distal end of the catheter, but also along the length of the catheter.

The method according to the invention proves to be particularly advantageous in the use of an electrode catheter, because such intravascular electrode catheters are introduced into the human body, for example for pacemaker therapy or to defibrillate the heart, as permanent implants, thereby giving rise in the case of explantation of the catheter to the initially cited problems which are so easily and effectively solved with the aid of the method according to the invention.

In the arrangement according to the invention for implanting or explanting the catheter, the catheter is oscillated so as to impart a transverse movement at least at the catheter tip by a mechanical oscillator attached to the catheter, such as an electromechanical transducer arranged in the interior of the catheter. The electromechanical transducer is set into an oscillating movement by an electric drive signal which is transmitted to the catheter at the site or sites at which the electromechanical transducer is arranged in the interior of the catheter.

The electromechanical transducer can be an integral component of the catheter, without requiring a special design of the catheter, and is preferably arranged on a control wire which can be introduced at the proximal end of the catheter through a channel extending in the interior of the catheter to its distal end.

The electromechanical transducer is preferably a piezoelectric element which can be particularly simply matched to the structural dimensions of the catheter and which is particularly simple to drive electrically.

In a particularly simple embodiment for setting the catheter into an oscillating movement transverse to its longitudinal extent, the drive device is arranged at the proximal end of the catheter, and a control wire is connected to the drive device, which extends through a channel in the interior of the catheter to the distal end thereof and which is set into a translatory or rotary movement by the drive device. Means are provided for converting the translatory or rotary movement of the control wire into an oscillating movement of prescribed regions of the catheter transverse to its longitudinal extent. The catheter is thereby set into the oscillating movement in a locationally defined fashion, at the predetermined sites at which the means for converting the movement of the control wire into the movement of tile catheter are provided.

The means for converting the translatory or rotary movement of the control wire into a movement of the catheter transverse to its longitudinal direction are preferably formed by outer contours of the control wire which deviate eccentrically from the normal rectilinear course of the control wire. Such outer contours deviating from the rectilinear course of the control wire can, for example, be by lug-shaped configurations formed by eccentrically arranged partially thickened spots on the control wire. Since the catheter is elastic, it follows in its course the outer contours of the control wire, so that in the event of movement of the control wire relative to the catheter the catheter is set, in the regions in which the control wire deviates from the rectilinear course, into a movement transverse to its longitudinal extent. This transverse movement can be further amplified by providing the catheter in its interior with leading surfaces, extending obliquely relative to its longitudinal extent, for the eccentric outer contours of the control wire.

The outer contours of the control wire which deviate eccentrically from the rectilinear course preferably take the form of bends in the control wire, as a result of which a configuration of the control wire is achieved which is as simple as possible. In this case, the first step in introducing of the control wire into the interior of the catheter is to push a tube which is flexible, but stiffer by comparison with the control wire onto the control wire, so that the control wire temporarily assumes a straight configuration by virtue of being confined in the tube. The tube together with the control wire, now extending rectilinearly in the tube are then pushed together into the catheter. Thereupon only the tube is withdrawn from the catheter, the control wire then re-assumes its bent form in the catheter.

DESCRIPTION OF THE PREFERRED EMBODIMENTS

Figure 1:
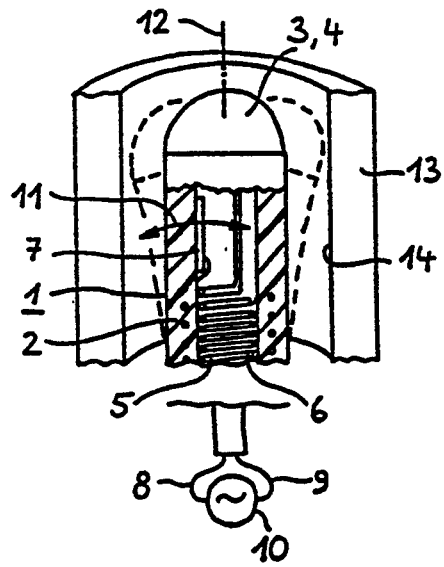
FIG. 1 shows a cross-section through the distal end of an electrode catheter having an electromechanical transducer as an integral component of the catheter, constructed in accordance with the principles of the present invention.

FIG. 1 shows, in a simplified representation, a cross-section through the distal end region of an electrode catheter 1 constructed in accordance with the principles of the present invention. The electrode catheter 1 has an elongated, flexible, electrically insulating sheath 2 which carries an electrode head 4 at the distal end 3 (distal relative to a stimulation device (not shown) to be connected at the opposite end). Connected to the electrode head 4 is an electrode lead 5 which extends through a channel 6 in the interior of the catheter 1 from its opposite proximal end (not shown here) and is connected there to a connecting element. Arranged in the region of the distal end 3 of the catheter 1 is an electromechanical transducer 7, which is a piezoelectric bending transducer, and which bears against the channel wall in the interior of the catheter 1. The electromechanical transducer 7 is provided with leads 8 and 9 which are connected at the proximal end of the catheter 1 to an a.c. voltage generator 10. The a.c. voltage generator 10 applies an a.c. voltage to the electromechanical transducer 7 which is converted by the transducer 7 into an oscillating bending movement 11. This bending movement 11 is transmitted to the flexible insulating sheath 2 of the catheter 1 and sets at least the distal end region of the catheter 1 the latter into a corresponding oscillating movement performed transverse to the longitudinal extent 12 of the catheter 1; the longitudinal extent 12 of the catheter 1 is indicated by its longitudinal axis. Due to the oscillating transverse movement 11 of the catheter 1, the catheter is continuously repelled from the inner wall 13 of the blood vessel 14 accommodating it. Given a sufficiently high frequency the catheter 1 effectively floats on the internal wall 14 of the blood vessel 13.

Figure 2:
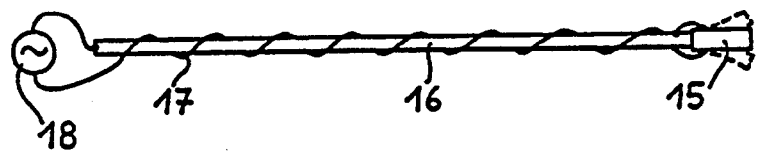
FIG. 2 shows a control wire, which can be introduced into the interior of a catheter, having an electromechanical transducer, in accordance with the principles of the present invention.

FIG. 2 shows as an alternative exemplary embodiment to FIG. 1 wherein an electromechanical transducer 15 at the end of a control wire 16 which is pushed from the proximal end of the catheter into the channel 6 (cf. FIG. 1) of the catheter 1, so that the electromechanical transducer 15 comes to lie in the region of the distal end 3 of the catheter 1. The electromechanical transducer 15 is provided with leads, one of which one is formed by the control wire 16 and the other by a lead 17 which is insulated with respect to the control wire 16. Driving the electromechanical transducer 15 is performed, as in the example according to FIG. 1, by an ac voltage generator 18.

Figure 3A:
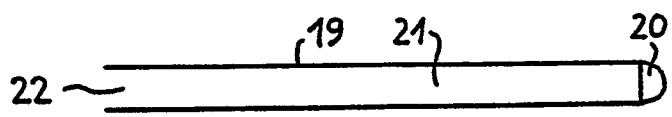
FIGS. 3A–3D respectively show an electrode catheter, a simply bent control wire which can be introduced into the catheter by means of a tube, and a drive device for connection to the control wire in the lie region of the proximal end of the catheter, in accordance with the principles of the present invention.
Figure 3B:
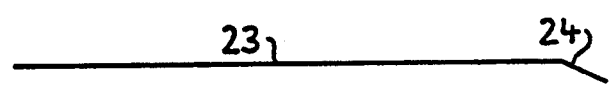
Figure 3C:
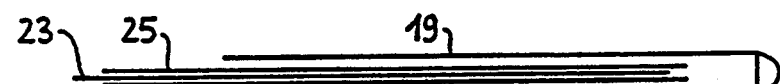
Figure 3D:
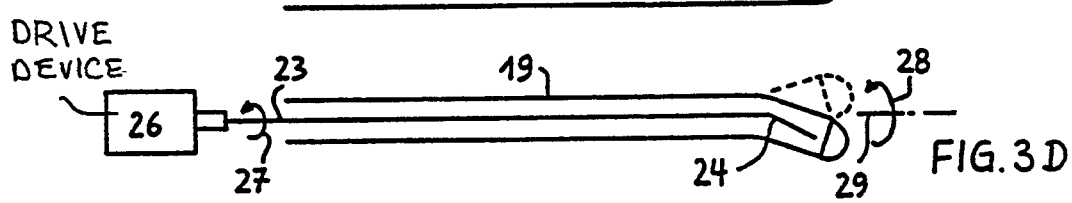

FIG. 3A shows, in a simplified way, a flexible electrode catheter 19 having an electrode head 20 at the distal end and a channel 21, which has an opening 22 at its proximal end extending through the catheter 19 to the distal end thereof. Represented in FIG. 3B is a likewise flexible control wire 23 which is provided for the purpose of insertion into the catheter 19. The control wire 23 has, at its end which comes to lie in the region of the distal end of the catheter 19, a bend 24 which deviates from the otherwise rectilinear course of the control wire 19. As FIG. 3C shows, the first step in introducing the control wire 23 into the catheter 19 is to push a tube 25 which is flexible, but stiffer in comparison with the control wire 23, onto the control wire 23, so that the control wire 23 is temporarily straightened in the region of its end 24 by confinement in the relatively-more-stiff tube 25. Subsequently, the control wire 23 is introduced into the catheter 19 together with the tube 25 which has been pushed there over. When, as shown in FIG. 3D, the tube 25 is then withdrawn from the catheter 19 the control wire 23 again assumes the prescribed bend 24 at its end in the catheter 19 and bends the catheter 19 in an appropriate way. At the proximal end of the catheter 19 a drive device 26, such as an electric motor, is now connected to the control wire 23 and sets the control wire 23 into a rapid rotary movement indicated by arrow 27. Due to the rotary movement of the control wire 23, the catheter 19 is set in the region of the bend 24 into a circular movement, performed transverse to the longitudinal extent of the catheter 19, about the longitudinal axis 29 of the catheter 19. By contrast with the control wire 23, the catheter 19 does not itself rotate.

Figure 4:
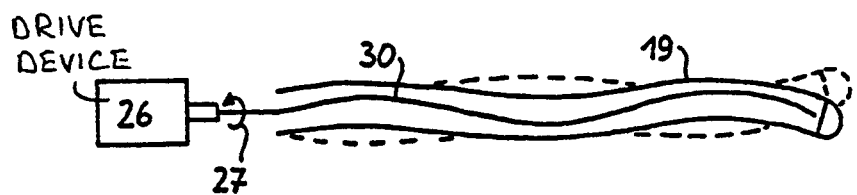
FIG. 4 shows the arrangement according to FIG. 3D having a multiply bent control wire.

The arrangement represented in FIG. 4 differs from the arrangement according to FIG. 3D only in that the control wire 30 in the catheter 19 is multiply bent in the direction of its longitudinal extent, so that the catheter 19 is bent in a corresponding way. The rotary movement 27 transmitted from the drive device 26 to the control wire 30 is thus converted into an undulating transverse movement of the catheter 19. As a result, the friction between the catheter 19 and the blood vessel respectively accommodating the catheter 19 is reduced not only in the region of the distal end of the catheter 19 but also along its longitudinal extent.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for facilitating movement of a catheter having a proximal end and a distal end through a blood vessel in a direction substantially parallel to a longitudinal extent between said proximal and distal ends of said catheter, comprising the steps of:
   connecting said catheter to a mechanical oscillator; and
   oscillating said catheter with said oscillator to impart movement at least to said distal end of said catheter substantially transversely to said longitudinal extent for reducing friction between said catheter and said blood vessel.

2. A method as claimed in claim 1 wherein the step of connecting said catheter to a mechanical oscillator is further defined by disposing said mechanical oscillator at said distal end of said catheter.

3. A method as claimed in claim 2 wherein the step of disposing said mechanical oscillator at said distal end of said catheter is further defined by disposing said oscillator inside said catheter at said distal end thereof.

4. A method as claimed in claim 2 wherein the step of disposing said mechanical oscillator at said distal end of said catheter is further defined by disposing said mechanical oscillator exclusively at said distal end of said catheter.

5. A method as claimed in claim 4 wherein said mechanical oscillator comprises an electromechanical transducer, and further comprising the step of supplying drive signals to said electromechanical transducer via leads extending inside said catheter.

6. A method as claimed in claim 1 wherein said mechanical oscillator includes a control wire extending through said catheter and having at least one bent region, and wherein the step of oscillating said catheter is further defined by rotating said control wire inside said catheter to oscillate said catheter to impart movement at least to said distal end of said catheter substantially transversely to said longitudinal extent of said catheter.

7. A method as claimed in claim 6 comprising the additional steps of:
   inserting said control wire into a tube having a length substantially coextensive with said control wire, said tube being relatively stiffer than said control wire for temporarily straightening said control wire while said control wire is in said tube; and
   inserting said tube with said control wire therein into said catheter and withdrawing only said tube from said catheter prior to rotating said control wire.

8. A method as claimed in claim 1 wherein said mechanical oscillator includes a control wire extending through said catheter and having a plurality of bent regions, and wherein the step of oscillating said catheter is further defined by rotating said control wire to impart movement substantially transversely to said longitudinal extent of said catheter at said distal end of said catheter and at a plurality of regions of said catheter substantially coinciding with said bent regions of said control wire.

9. A method as claimed in claim 8 comprising the additional steps of:
   inserting said control wire into a tube having a length substantially coextensive with said control wire, said tube being relatively stiffer than said control wire for temporarily straightening said control wire while said control wire is in said tube; and
   inserting said tube with said control wire therein into said catheter and withdrawing only said tube from said catheter prior to rotating said control wire.

10. An apparatus for facilitating movement of a catheter through a blood vessel in a direction substantially parallel to a longitudinal extent of said catheter, said apparatus comprising:
    a catheter having a proximal end and a distal end with a longitudinal extent therebetween; and
    mechanical oscillator means comprising an electromechanical transducer disposed at said distal end of said catheter for oscillator said catheter to impart movement to at least said distal end of said catheter substantially transversely to said longitudinal extent of said catheter for reducing friction between said catheter and said blood vessel.

11. An apparatus as claimed in claim 10 wherein said electromechanical transducer comprises a piezoelectric transducer.

12. An apparatus as claimed in claimed 10 wherein said electromechanical transducer is disposed inside said catheter at said distal end of said catheter.

13. An apparatus as claimed in claim 12 wherein said electromechanical transducer comprises a piezoelectric transducer.

14. An apparatus for facilitating movement of a catheter through a blood vessel in a direction substantially parallel to a longitudinal extent of said catheter, said apparatus comprising:
    a catheter having a proximal end and a distal end with a longitudinal extent therebetween; and mechanical oscillator means comprising a control wire disposed inside said catheter co-extensive with said longitudinal extent and having a bend at an end thereof disposed at said distal end of said catheter, and means for rotating said control wire, for oscillating said catheter to impart movement to at least said distal end of said catheter substantially transversely to said longitudinal extent of said catheter for reducing friction between said catheter and said blood vessel.

15. An apparatus as claimed in claim 14 further comprising a tube removably insertable in said catheter with said control wire therein, said tube having a stiffness for temporarily straightening said control wire contained in said tube until withdrawal of said tube from said catheter.

16. An apparatus for facilitating movement of a catheter through a blood vessel in a direction substantially parallel to a longitudinal extent of said catheter, said apparatus comprising:

a catheter having a proximal end and a distal end with a longitudinal extent therebetween; and mechanical oscillator means comprising a control wire having a plurality of outer contours eccentrically deviating from a rectilinear course of said control wire, said control wire extending through said catheter between said proximal end and said distal end, and means for rotating said control wire in said catheter, for oscillating said catheter to impart movement to at least said distal end of said catheter substantially transversely to said longitudinal extent of said catheter for reducing friction between said catheter and said blood vessel.

17. An apparatus as claimed in claim 16 wherein said control wire comprises a wire having a plurality of bends therein forming said outer contours.

18. An apparatus as claimed in claim 17 wherein said means for oscillating comprises a control wire having a bend at an end thereof disposed at said distal end of said catheter.

* * * * *